United States Patent
Hanes

(10) Patent No.: US 7,108,720 B2
(45) Date of Patent: Sep. 19, 2006

(54) REDUCED WEAR ORTHOPAEDIC IMPLANT APPARATUS AND METHOD

(75) Inventor: Mark D. Hanes, Winona Lake, IN (US)

(73) Assignee: DePuy Products, Inc., Warsaw, IN (US)

( * ) Notice: Subject to any disclaimer, the term of this patent is extended or adjusted under 35 U.S.C. 154(b) by 388 days.

(21) Appl. No.: 10/403,921

(22) Filed: Mar. 31, 2003

(65) Prior Publication Data

US 2004/0193282 A1  Sep. 30, 2004

(51) Int. Cl.
*A61F 2/32* (2006.01)

(52) U.S. Cl. ............................... 623/22.21; 623/22.11; 623/22.18; 623/22.15

(58) Field of Classification Search ............. 623/22.11, 623/22.15–22.21, 22.24, 22.28–22.29, 35, 623/39, 40

See application file for complete search history.

(56) References Cited

U.S. PATENT DOCUMENTS

| | | | |
|---|---|---|---|
| 4,031,570 A | 6/1977 | Frey | |
| 4,851,006 A | 7/1989 | Tuke | |
| 5,358,529 A | 10/1994 | Davidson | |
| 5,549,697 A | 8/1996 | Caldarise | |
| 5,609,638 A | 3/1997 | Price et al. | |
| 5,641,323 A | 6/1997 | Caldarise | |
| 5,645,594 A | 7/1997 | Devanathan et al. | |
| 5,658,338 A * | 8/1997 | Tullos et al. | 623/22.39 |
| 5,788,916 A | 8/1998 | Caldarise | |
| 5,824,107 A * | 10/1998 | Tschirren | 623/22.28 |
| 5,879,400 A | 3/1999 | Merrill et al. | |
| 5,879,404 A | 3/1999 | Bateman et al. | |
| 5,879,406 A * | 3/1999 | Lilley | 623/22.15 |
| 5,938,702 A * | 8/1999 | Lopez et al. | 623/22.38 |
| 5,989,293 A | 11/1999 | Cook et al. | |
| 6,143,232 A | 11/2000 | Rohr | |
| 6,146,426 A | 11/2000 | Doyle | |
| 6,152,961 A * | 11/2000 | Ostiguy et al. | 623/22.28 |
| 6,184,265 B1 | 2/2001 | Hamilton et al. | |
| 6,368,354 B1 | 4/2002 | Burstein et al. | |
| 6,395,799 B1 | 5/2002 | Johnson | |
| 6,464,926 B1 | 10/2002 | Merrill et al. | |
| 6,488,731 B1 * | 12/2002 | Schultheiss et al. | 55/486 |
| 6,503,439 B1 | 1/2003 | Burstein | |
| 6,537,321 B1 * | 3/2003 | Horber | 623/22.22 |
| 6,610,097 B1 * | 8/2003 | Serbousek et al. | 623/22.24 |
| 2002/0049500 A1 | 4/2002 | Draenert | |
| 2002/0052659 A1 | 5/2002 | Hayes, Jr. et al. | |
| 2002/0107577 A1 | 8/2002 | Storer et al. | |
| 2002/0161448 A1 | 10/2002 | Hayes, Jr. et al. | |
| 2003/0171817 A1 * | 9/2003 | Rambert et al. | 623/22.17 |

(Continued)

FOREIGN PATENT DOCUMENTS

EP  0 552 949  7/1993

(Continued)

*Primary Examiner*—Eduardo C. Robert
*Assistant Examiner*—Mary Hoffman
(74) *Attorney, Agent, or Firm*—Maginot, Moore & Beck

(57) ABSTRACT

A prosthetic implant includes first, second and third components. The first component is configured to be disposed within the acetabulum. The second component is in a load bearing relationship with the first component, and is operable to rotate in a first axis of rotation. The second component is inhibited from movement in a second axis of rotation. The third component is in a load bearing relationship with the second component. The third component is operable to rotate in the second axis of rotation, but is inhibited from movement with the first axis of rotation.

16 Claims, 6 Drawing Sheets

U.S. PATENT DOCUMENTS

2004/0054418 A1 * 3/2004 McLean et al. .......... 623/22.17

FOREIGN PATENT DOCUMENTS

| EP | 0 613 667 | | 9/1994 | |
|----|-----------|---|--------|---|
| EP | 0 761 242 | | 3/1997 | |
| EP | 0 803 234 | | 10/1997 | |
| EP | 0 923 945 | | 6/1999 | |
| EP | 1 247 502 | | 3/2002 | |
| WO | WO 97/10776 | * | 9/1995 | .............. 623/22.17 |
| WO | WO 01/05337 | | 1/2001 | |
| WO | WO 02/00140 | | 1/2002 | |
| WO | WO 02/07652 | | 1/2002 | |
| WO | WO 02/09615 | | 2/2002 | |
| WO | WO 02/09616 | | 2/2002 | |

* cited by examiner

REDUCED WEAR ORTHOPAEDIC IMPLANT APPARATUS AND METHOD

FIELD OF THE INVENTION

The present invention relates generally to prosthetic orthopaedic implants, and more particularly, to joint prosthetic implants.

BACKGROUND OF THE INVENTION

Many orthopaedic procedures involve the implantation of prosthetic devices to replace badly damaged or diseased bone tissue. Common orthopaedic procedures that involve prosthetic devices include total or partial hip, knee and shoulder replacement. Hip replacement involves total or partial replacement of the hip ball and socket joint.

A total hip replacement procedure typically involves the implantation of two main component systems: the femoral component and an acetabular component. The femoral component includes a rigid stem that is anchored within the existing femur and also includes a head that replaces the natural hip joint femoral head. The acetabular component is secured within the acetabulum of the patient and serves as a bearing surface for the head of the femoral component.

Historically, acetabular components have a generally rounded outer surface that is secured to natural bone within the acetabulum and include a roughly hemispherical interior surface for receiving a round femoral head. The femoral head and hemispherical interior surface form a ball and socket joint that approximates the natural hip joint. The acetabular component often includes an outer shell and one or more intermediate components, or liners. The outer shell is anchored or otherwise secured to the bone tissue within the acetabulum and the liner or liners are disposed within the outer shell. The liner(s) form the bearing surface for the pivoting femoral head.

Regardless of the precise structure, prior art hip prostheses typically employ the ball and socket or spherical rotation joint to approximate anatomical hip movement.

A set of problems associated with hip prosthesis arises from the wear of the hip implant bearings. In particular, extensive use of a prosthetic hip can cause the bearings to wear, releasing debris in and around the surrounding tissue. For example, a typically total hip prosthesis includes a metal or ceramic outer shell, an ultra high molecular weight polyethylene (UHMWPE) liner, and a cobalt-chromium or ceramic femoral head. In such a prosthesis, it has been observed that the bearing surface of the UHMWPE liner wears, thereby producing particulate debris.

Particulate from UHMWPE wear can interfere with the motion capabilities of the prosthetic and furthermore can create an adverse biological reaction. Small debris can produce osteolysis (bone resorption) and/or cause an immune response.

Similarly, if a metal liner is instead used, the wear from the metal on metal bearings (metal liner to metal femoral head) can release increased levels of metal ions in the body which can produce adverse health effects. Ceramic liners do not produce metal ions, but are expensive and can fail in a brittle manner, which is highly undesirable.

Accordingly, there exists a need for reducing the adverse affects caused by wear of the bearing surfaces of total hip replacement prostheses.

SUMMARY OF THE PRESENT INVENTION

The present invention addresses the above needs, as well as others, by providing a prosthetic implant arrangement that includes multiple articulating surfaces that allow movement about different rotational axes. Each of the multiple articulating surfaces is restricted from full spherical pivotal motion, thereby reducing cross-shear, which has been found to reduce wear. Preferably, at least two articulating surfaces are provided, each allowing rotation about an orthogonal axis. With even two of such articulating surfaces, nearly all anatomical hip movements are possible.

A first embodiment of the invention is a prosthetic implant that includes first, second and third components. The first component is configured to be disposed within the acetabulum. The second component is in a load bearing relationship with the first component, and is operable to rotate in a first axis of rotation. The second component is inhibited from movement in a second axis of rotation. The third component is in a load bearing relationship with the second component. The third component is operable to rotate in the second axis of rotation, but is inhibited from movement with the first axis of rotation.

Another embodiment of the invention is an implant having at least a first component, a second component and a third component. At least two of the first, second and third components include annular grooves, each annular groove receiving at least one protruding feature of an adjacent component to allow annular movement of the at least one protruding feature within the groove. The annular grooves have nonparallel axes of rotation.

The advantages of the present invention may suitably have application in other orthopaedic implant devices. In particular, a joint prosthesis having two restricted bearing surfaces could have application in shoulder replacement, although shoulders do not typically employ the same degree of hemispherical motion as hips.

The above described features and advantages, as well as others, will become more readily apparent to those of ordinary skill in the art by reference to the following detailed description and accompanying drawings.

DETAILED DESCRIPTION

Figure 1:
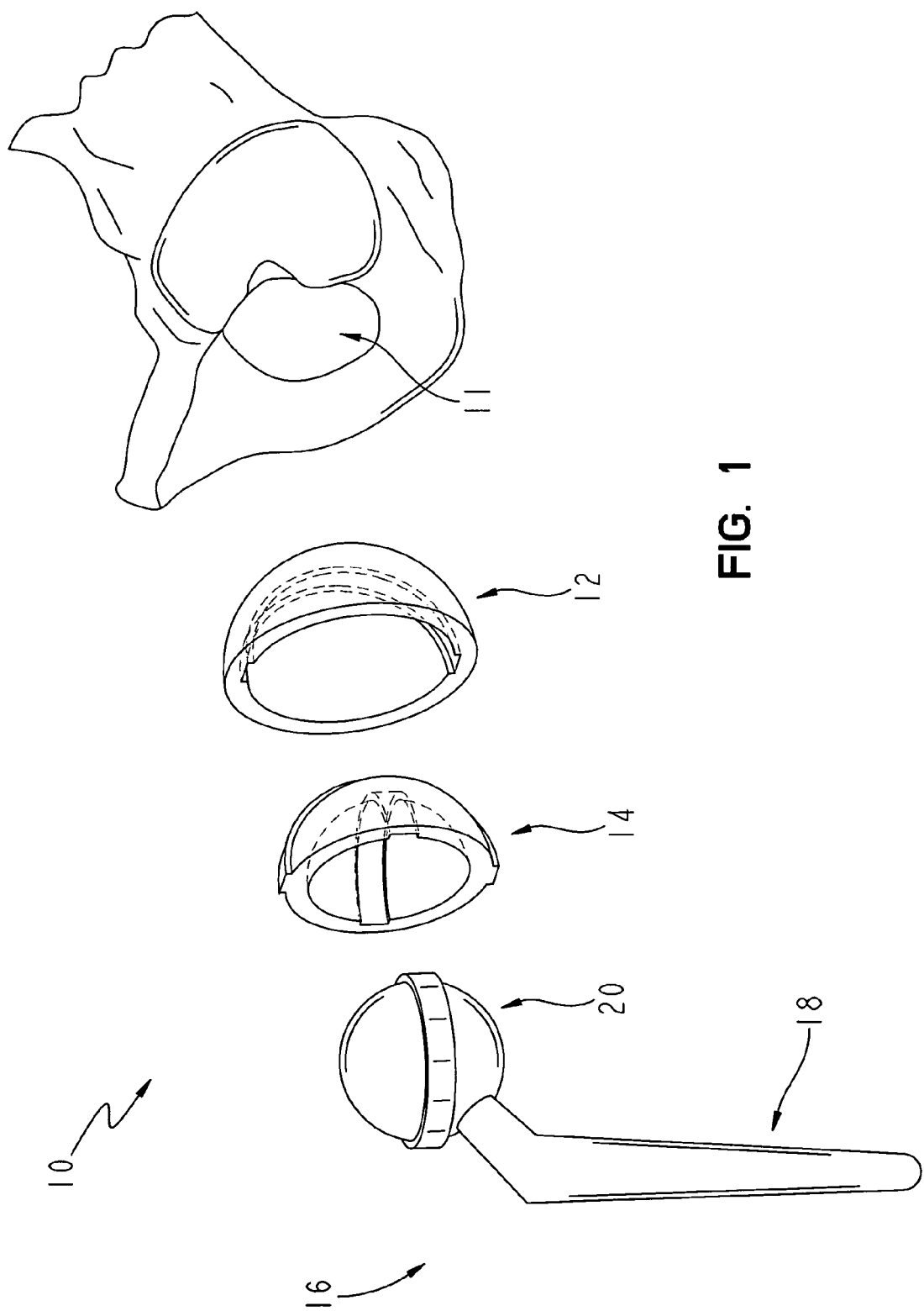
FIG. 1 shows an exploded perspective view of an exemplary hip implant arrangement according to the present invention as well as a fragmentary bone structure showing an acetabulum in which the arrangement may be implanted.

FIG. 1 shows an exploded perspective view of an exemplary hip implant arrangement 10 according to the present invention as well as a fragmentary bone structure showing an acetabulum 11 of a human patient The hip arrangement includes an acetabular shell 12, a liner 14 and a femoral component 16. The acetabular shell 12 is generally configured to be received in the acetabulum 11 of a patient, and the liner 14 is configured to be received in the acetabular shell 12. The femoral component 16 includes a femoral stem 18 and a femoral head 20. The femoral stem 18 is configured to be received into or at least supported by the femoral bone tissue of the patient, not shown, and the femoral head 20 is configured to be received in the liner 14.

Figure 2:
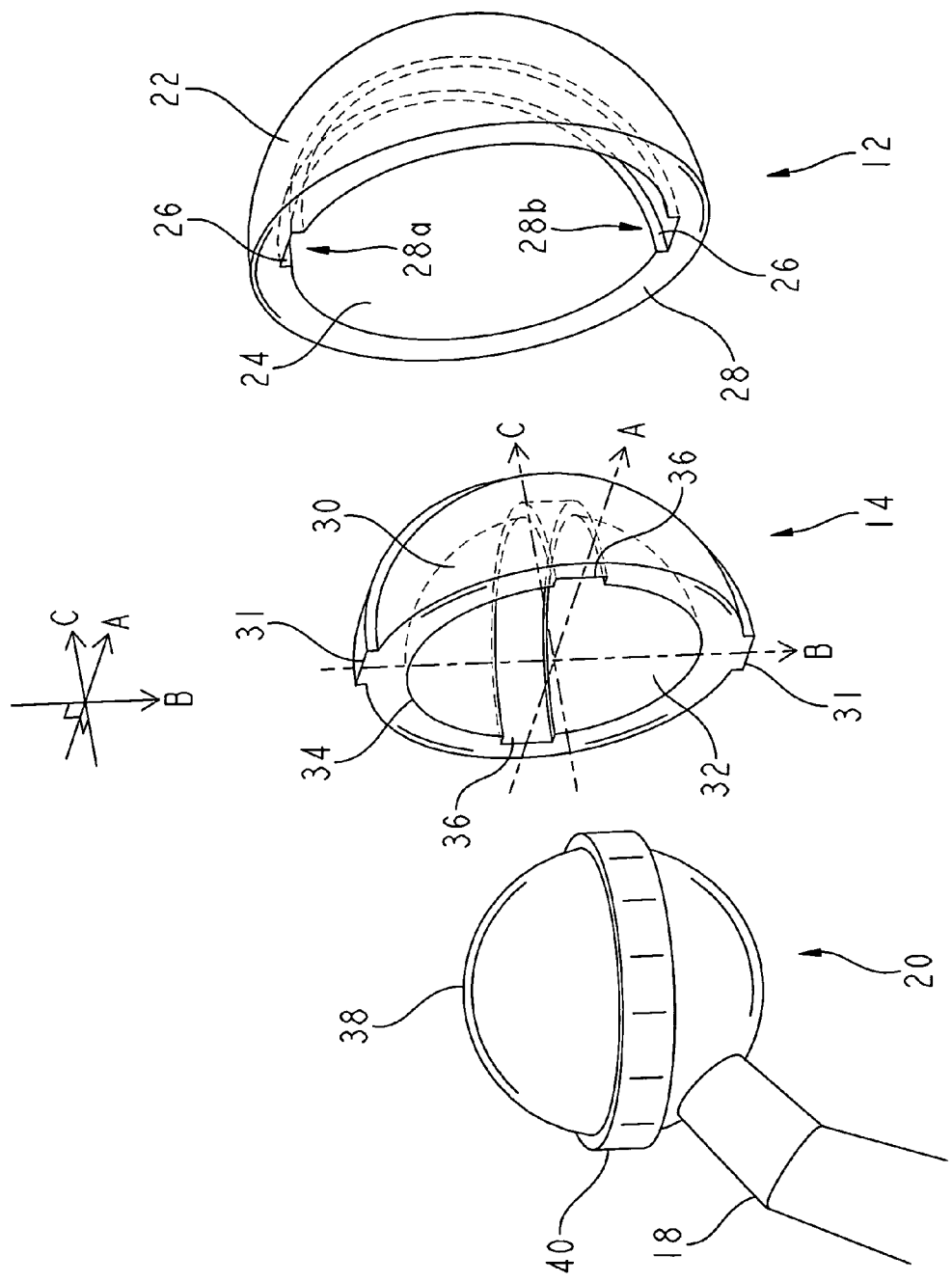
FIG. 2 shows a fragmentary, enlarged, perspective, exploded view of the implant arrangement of FIG. 1.

FIG. 2 shows a fragmentary, enlarged and exploded view of the implant arrangement 10 without the patient bone structure. As shown in both FIG. 1 and FIG. 2, the acetabular shell 12 includes an outer surface 22 having a generally rounded shape, preferably hemispherical or at least partially spherical. The outer surface 22 is configured to secure to the acetabulum 11 (see FIG. 1) using any well known method and/or structure. The acetabular shell 12 further includes an inner surface 24 that is generally partially spherical in shape. In a first embodiment described herein, at least the inner surface 24 forms slightly more than a hemisphere (i.e. forms more than half of sphere) so that the diameter of the annular rim 28 at the periphery of the inner surface 24 is less than the diameter of the widest part of the inner surface 24. The inner surface 24 diameter is smaller in order to create an interference to retain the liner 14 within the inner surface 24 of the shell 12, as will be discussed further below.

Formed in the inner surface 24 is an annular groove or channel 26 that extends around a first axis A. The channel 26 effectively bisects the inner surface 24 and has a depth that is less than the thickness defined by the distance between the inner surface 24 and the outer surface 22. In the embodiment described herein, the channel 26 extends from a first side 28a of the annular rim 28, through the inner surface 24 about the axis A, and to an opposing side 28b of the annular rim 28.

The acetabular shell 12 is preferably formed from metal or ceramic material. Suitable materials are well known in the art. An exemplary acetabular shell 12 may be constructed of a higher hardness alloy, such as an alloy of cobalt and chromium. For example, the acetabular shell 12 may be constructed of CoCrMo.

The liner 14 includes an outer surface 30 having a generally hemispherical or at least partially spherical shape which is slightly smaller than the inner surface 24 of the acetabular shell 12. The outer surface 30 is configured to be received by the inner surface 24 of the acetabular shell 12. The diameter of the outer surface 30 at its widest (not including the protrusion 31, discussed below) is greater than the diameter of the annular rim 28 of the inner surface 24 of the acetabular shell 12. As a consequence, the liner 14 is retained within the acetabular shell 12 but may generally rotate.

The outer surface 30 further includes an outwardly extending annular protrusion 31 that is configured to be received by the annular channel 26 of the acetabular shell 12. In the exemplary embodiment described herein, the annular protrusion 31 extends completely around the outer surface 28 in an annular linear path about the axis A and such that the protrusion 31 approximately bisects the outer surface 28. The annular channel 26 and the annular protrusion 31 cooperate to allow the liner 14 to rotate at least partially about the axis A.

The liner 14 further includes an inner surface 32 that is generally partially spherical in shape. In a first embodiment described herein, the inner surface 32, similar to the inner surface 24 of the acetabular shell 12, defines a portion of a sphere slightly greater than a hemisphere (i.e. forms more than half of a sphere) so that the diameter of the annular rim 34 of the inner surface 32 is less than the diameter of the widest portion of the inner surface 32. As with the acetabular shell 12, such configuration of the inner surface 32 of the liner 14 allows the liner 14 to retain the femoral head 20 therein, as will be discussed further below.

Bisecting the inner surface 32 is an annular groove or channel 36 that extends in a annular linear path about a second axis B. The axes A and B are not parallel, and in the exemplary embodiment of FIGS. 1 and 2, are perpendicular or orthogonal to each other. The channel 36 has a depth that is less than the thickness defined by the distance between the inner surface 32 and the outer surface 30.

The liner 14 is preferably formed from a polymeric material. Suitable materials are well known in the art. An exemplary liner may be formed from UHMWPE or highly cross-linked UHMWPE.

The femoral head 20 includes an outer surface 38 having a generally spherical or at least partially spherical shape which is slightly smaller than, and is configured to be received by, the inner surface 32 of the liner 14. The diameter of the outer surface 38 at its widest is greater than the diameter of the annular rim 34 of the inner surface 32 of the liner 14. As a consequence, the femoral head 20 is retained within the liner 14 but may generally rotate.

The outer surface 38 further includes an outwardly extending annular protrusion 40 that is configured to be received by the annular channel 36 of the liner 14. The annular channel 36 and the annular protrusion 40 allow the femoral head 20 to rotate at least partially about the axis B. The combined rotational action of the femoral head 20 about axis B and the liner 14 about the axis A provides a large range of motion of the femoral component 16 relative to the acetabular shell 12.

In an exemplary implementation, the acetabular implant arrangement 10 is used in a total hip replacement procedure. Referring again to FIGS. 1 and 2, a surgical method for implanting the implant basically involves assembling the components 12, 14 and 16 of the arrangement 10 and implanting the arrangement 10 within the acetabulum 11 of the patient while supporting the femoral component 16 within the femoral bone tissue.

In further detail, a reamer, not shown, is typically used to ream or otherwise cut the acetabulum 11 in order to form a hemispherically shaped cavity. The surgeon may then implant either final components, or trial fit components. Trial fitting is well known in the art, and assists the surgeon in final preparation of the acetabulum and in choosing the proper sizes of the various components of the arrangement 10.

After suitable trialing, the trial implant is removed and the surgeon may then implant the acetabular shell 12 into the acetabulum 11. The acetabular shell 12 may be press fit, bolted or cemented into the acetabulum 11 as is known in the art.

In a first exemplary procedure, the acetabular shell 12 is implanted into the acetabulum 11 separately and then the liner 14 is pressed into the acetabular shell 12 in vivo. The liner 14 is pressed into the shell 12 such that the larger diameter of the outer surface 30 of the liner 14 passes the smaller diameter of the annular rim 28 of the acetabular shell 12. The liner 14 is aligned so that the protrusion 31 is received within the channel 26 of the shell 12. When the liner 14 is so implanted, the protrusion 31 and the channel 26 cooperate to allow the liner 14 to rotate about the axis A within the acetabular shell 12. However, the protrusion 31 and the channel 26 also cooperate to inhibit movement of the liner 14 about any other axes, including the axis B. Thus, the implanted shell 12 is stationary and the liner 14 is capable only of annular linear movement about the axis A.

Thereafter, the surgeon secures the femoral head 20 within the liner 14. The femoral stem 18 may already be implanted within the femoral bone tissue, not shown. To secure the femoral head 20 within the liner 14, the femoral head 20 is pressed into the liner 14 such that the larger diameter of the outer surface 38 of the femoral head 20 passes the smaller diameter of the annular rim 34 of the liner 14. The femoral head 20 and liner 14 are aligned such that the channel 36 of the liner 14 receives the protrusion 40. When the femoral head 20 is so implanted, the protrusion 40 and the channel 36 cooperate to allow the femoral head 20 to rotate about the axis B with respect to the liner 14. However, the protrusion 40 and the channel inhibit movement of the femoral head 20 about the axis A or any other axis with respect to the liner 14. The combination of the rotation of the liner 14 about the axis A and the femoral head 20 about the axis B provides pivotal motion equivalent to that of a ball and socket joint.

In the embodiment described above, the components of the implant arrangement 10 are assembled in vivo. Alternatively, any two (or all three) components may be instead assembled external to the acetabulum 11 prior to implantation.

It will be appreciated that each articulating load bearing surface of the assembled implant arrangement 10 of FIG. 1 is exposed only to linear annular motion. It has been found that such restriction of the degrees of freedom of the articulating surfaces reduces the tendency to produce wear particulate or debris. (See, e.g., Reference 1: D. E. McNulty, S. W. Swope, D. D. Auger, and T. S. Smith, "The Effect of Crosslinking UHMWPE on In Vivo Wear Rates of Fixed and Mobile-bearing Knees", Crosslinked and Thermally Treated Ultra-high Molecular Weight Polyethylene for Joint Replacements, ASTM STP 1445, S. M. Krutz, R. Gsell, and J. Martell, Eds., ASTM International, West Conshohocken, Pa. 2003; and Reference 2: T. J. Joyc, D. Monk, S. D. Scholes, A. Unsworth, "A multi-directional wear screening device and preliminary results of UHMWPE against stainless steel", Bio-Medical Materials and Engineering, v. 10, #3-4, 2000, pg 241.) The disclosures of each of the two above-identified reference articles are hereby totally incorporated by reference in their entirety.

A potential theoretical explanation for this reduced tendency relates to the alignment of polymer chains in the liner 14 along the annular path of movement. In general, the frictional movement of a bearing against a polymer bearing tends to cause realignment of surface polymer chains on the polymer bearing. If the polymer bearing is exposed to an unrestrained multiaxis range of motion, the polymer chains would attempt to realign constantly with each different movement direction. Such constant attempts to realign the polymer chains can weaken and break the polymer chains. By contrast, if only linear annular movement is permitted, the polymer chains do not have to realign and are less prone to weakening.

It will be appreciated that the principles of the invention and at least some of the benefits may be carried out in a number of different ways. In one alternative, the annular channels and their corresponding annular protrusions may be juxtaposed on their respective bearing surfaces. For example, the annular channel 26 may be disposed on the outer surface 30 of the liner 14 and the corresponding annular protrusion 31 may be disposed on the inner surface 24 of the acetabular shell 12s. In another example, while the protrusions 31 and 40 are shown extending continuously around their respective surfaces, the protrusions may only extend partially around, and/or consist of multiple smaller, annularly spaced apart protrusions.

In addition, at least one protrusion may be in the form of a pin that is rotatable within one of the grooves. By using a pin that is rotatable within the groove, the component of the implant on which the pin is disposed may both pivot or rotate about the axis defined by the groove in the adjoining component and rotate about the axis of the pin.

Figure 4:
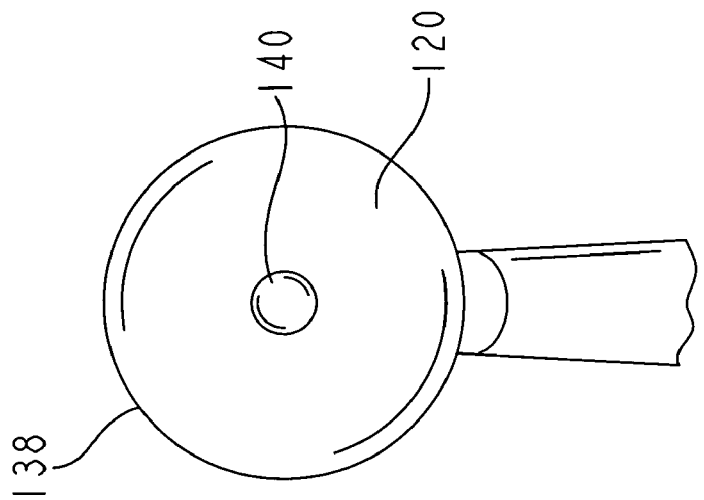
FIG. 4 shows a fragmentary front plan view of the alternative femoral component of FIG. 3.
Figure 3:
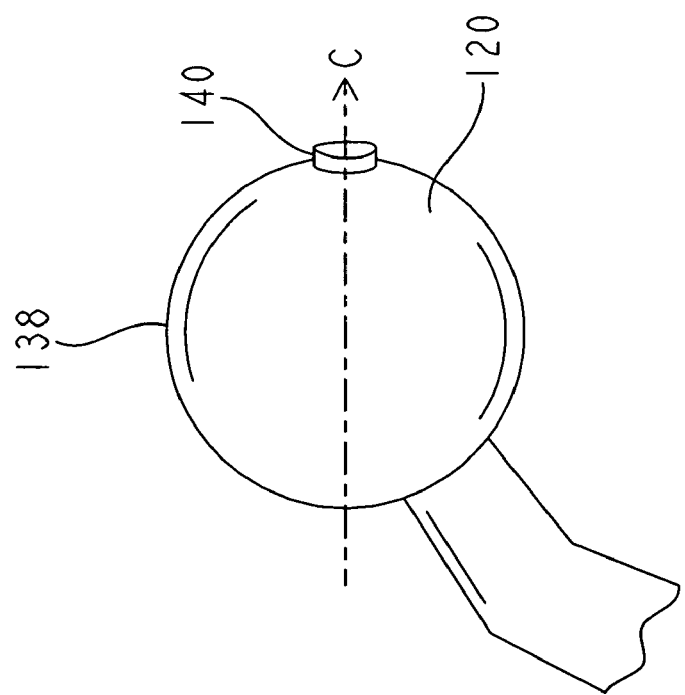
FIG. 3 shows a fragmentary perspective view of an alternative femoral component for use in the implant arrangement of FIG. 1.

For example, FIGS. 3 and 4 show an alternative embodiment of a femoral head 120 that may be used as a replacement for the femoral head 20 in the implant arrangement 10 of FIGS. 1 and 2. Referring to FIGS. 1, 2, 3 and 4 simultaneously, the femoral head 120 has a generally spherical outer surface 138 that includes a pin protrusion 140. The pin protrusion 140 has an axial dimension along the axis C that is configured to be received by the annular channel 36 on the inner surface 32 of the liner 14. The pin protrusion 140 is rounded when viewed from the front (See FIG. 4), and has a diameter less than the width of the annular channel 36. As a consequence, the pin protrusion 140 may rotate about the axis C, as well as travel in the annular channel 36 about the axis B (see FIG. 2).

Figure 6:
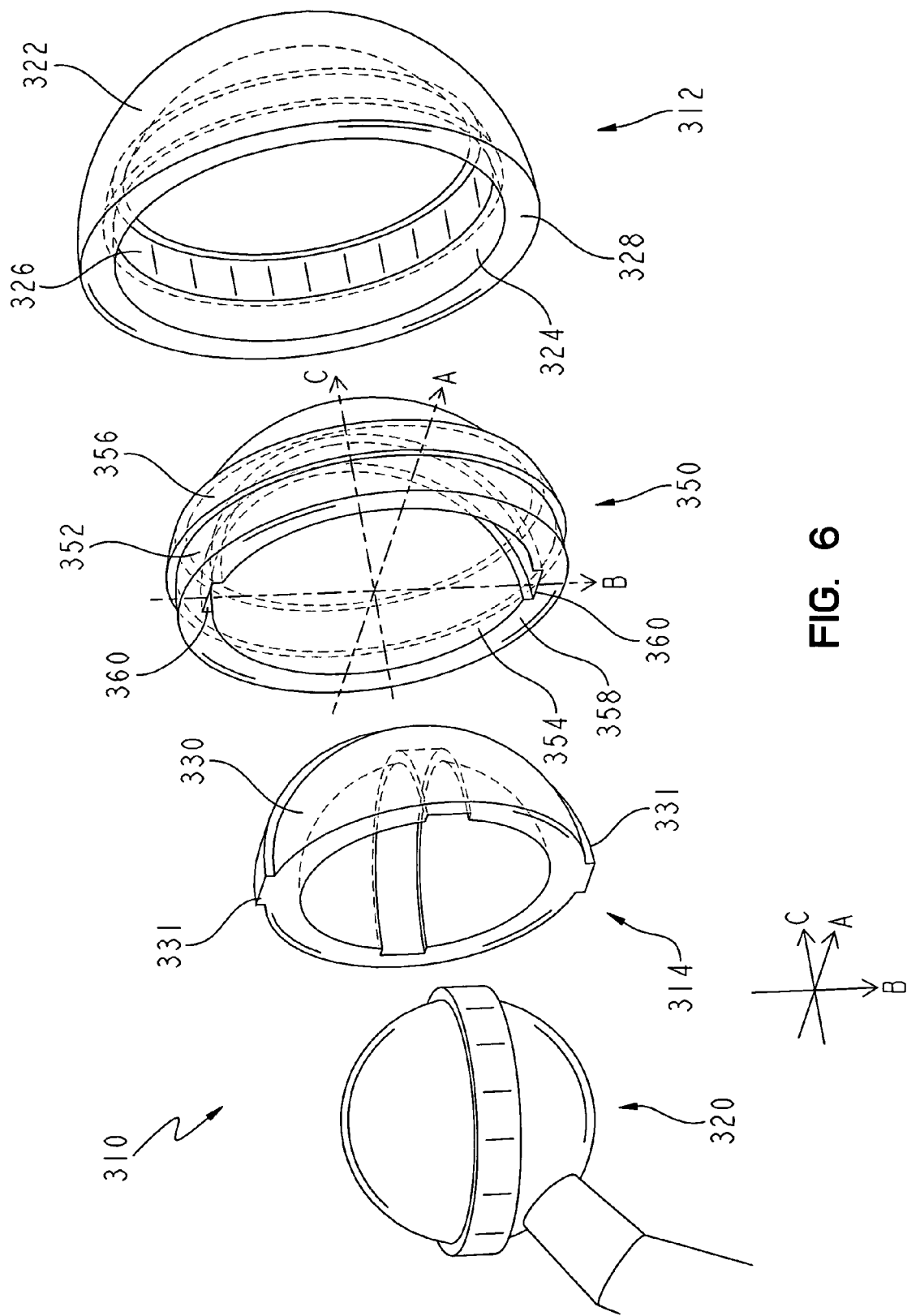
FIG. 6 shows a fragmentary, perspective, exploded view of an alternative implant arrangement according to the invention.

The added rotational capability about the axis C may improve the range of anatomical motion. One drawback about allowing the femoral head 120 to rotate about both the B and C axes is that some of the benefits of restricting the bearing surfaces to unidimensional motion can be compromised. However, the axis C may be chosen to constitute an axis of rotation that is minimally necessary for natural hip motion. As a consequence, the negative wear effects of multidimensional movement of the bearing surfaces (surfaces 138 and 32) are limited. FIG. 6, discussed further below, provides another alternative embodiment that allows a full range of motion about a third axis of rotation without exposing any bearing surface to multidimensional motion.

Referring again to FIGS. 3 and 4, it will be appreciated that the pin protrusion 140 need not be any particular configuration, so long as its width or radial dimensions are less than the width of the channel 36. Accordingly, the pin protrusion 140 may be polygonal or any other suitable shape.

It is noted that the two axes of rotation of the embodiment of FIGS. 1 and 2 are perpendicular or orthogonal with respect to each other. While the use of two (or three) perpendicular axes allows for a maximum range of motion, it may be preferable in some cases to uses two axes of rotation that are skewed from perpendicular. For example, the angle between the axes of rotation between bearing surfaces may be skewed to optimize alignment of the two axes for the most common types of hip joint movement. In particular, two axes of rotation may be chosen such that the number of hip movements that require only one of the bearing surfaces to rotate is optimized.

Figure 5:
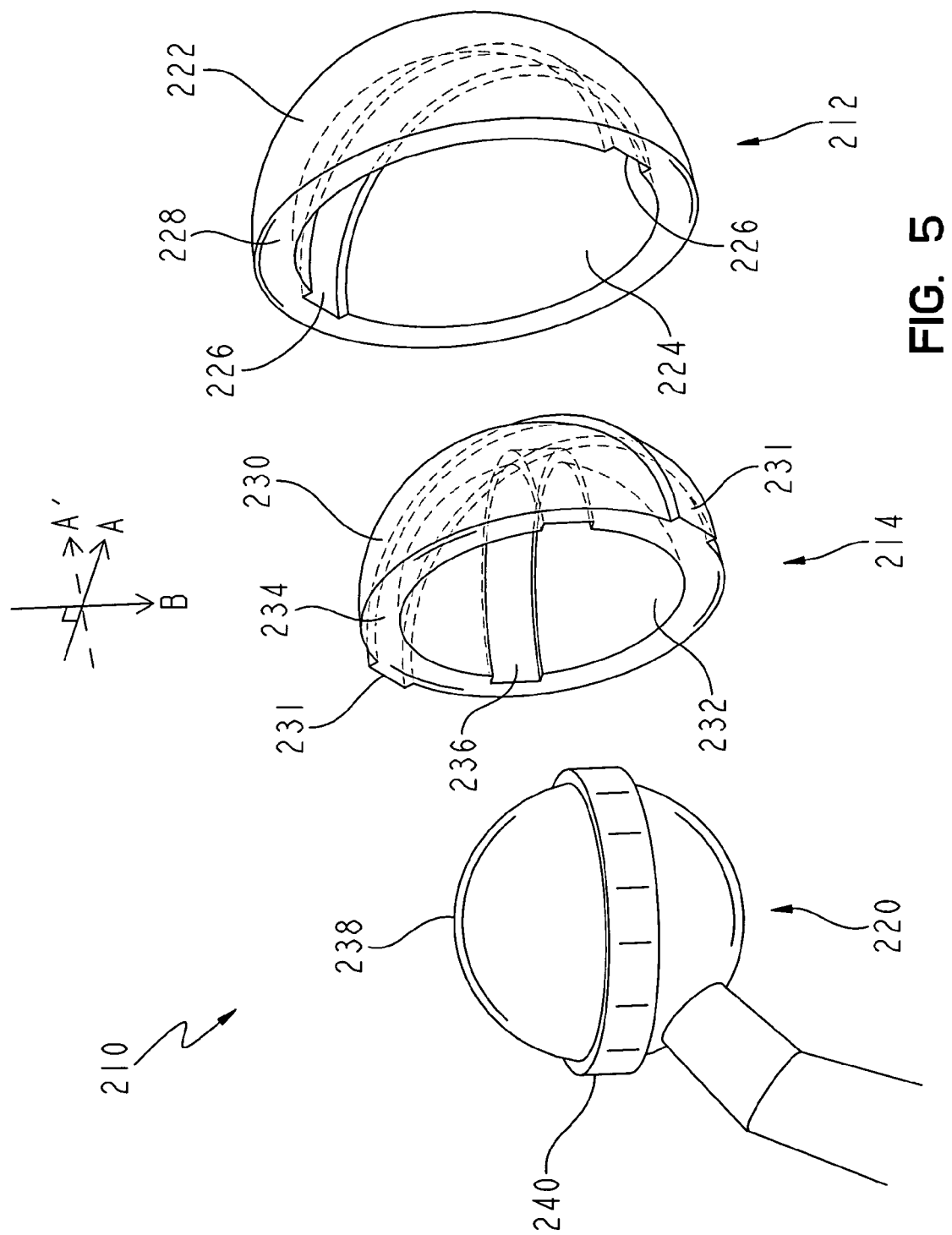
FIG. 5 shows a fragmentary, perspective, exploded view of an alternative implant arrangement according to the invention.

An example of an implant arrangement having skewed axes of rotation is shown in FIG. 5. The exemplary embodiment of the implant arrangement 210 of FIG. 5 includes an acetabular shell 212, a liner 214 and a femoral head 220. The femoral head 220 may suitably have the same structure as the femoral head 20 (or 120) of FIGS. 1 and 2 (or FIGS. 3 and 4).

The acetabular shell 212 is similar to the shell 12 of FIGS. 1 and 2 and includes an outer surface 222 having a rounded shape. The outer surface 222 is configured to secure to the acetabulum 11 (see FIG. 1) using any well known method and/or structure. The acetabular shell 212 further includes an inner surface 224 that is generally partially spherical in shape. In the embodiment of FIG. 5, the inner surface 224 also forms more than half of a sphere so that the diameter of the annular rim 228 of the inner surface 224 is less than the diameter of the widest portion of the inner surface 224. The inner surface 224 has a smaller diameter in order to allow the inner surface 224 to retain the liner 214 therein.

The inner surface 224 includes an annular groove or channel 226 that extends around an axis A'. The axis A' is not perpendicular to the axis B. The channel 226 is otherwise identical in structure to the channel 26 of FIG. 2. In the embodiment described herein, the axis A' is slightly (less than 20°) skewed from being perpendicular to the axis B.

The liner 214 includes an outer surface 230 having a generally hemispherical or at least partially spherical shape which is slightly smaller than the inner surface 224 of the acetabular shell 212. The outer surface 230 is configured to be received by the inner surface 224 of the acetabular shell 212. As with the outer surface 30 of the liner 14 of FIG. 2, the diameter of the outer surface 230 at its widest is greater than the diameter of the annular rim 228 of the inner surface 224 in order to be retained thereby.

The outer surface 230 further includes an outwardly extending annular protrusion 231 that is configured to be received by the annular channel 226 of the acetabular shell 212. In the exemplary embodiment described herein, the annular protrusion 231 extends completely around the outer surface 230 about the axis A'. The annular channel 226 and the annular protrusion 231 cooperate to allow the liner 214 to rotate at least partially about the axis A', but inhibit movement about other axes.

The liner 214 further includes an inner surface 232 that is generally partially spherical in shape. In the embodiment of FIG. 5, the inner surface 232 extends beyond the midpoint of a sphere (i.e. forms more than half of a sphere) so that the diameter of the annular rim 234 of the inner surface 232 is less than the diameter of the sphere partially defined by the inner surface 232. The inner surface 232 extends past the midpoint of the sphere in order to allow the inner surface 232 to retain the femoral head 220 therein.

Bisecting the inner surface 232 is an annular groove or channel 236 that extends around the axis B. The axes A' and B are neither parallel nor perpendicular, but cooperate to allow for combined motion along two axes A' and B. The combined motion provides a restricted ball and socket type of motion. The channel 236 has a depth that is less than the thickness defined by the distance between the inner surface 232 and the outer surface 230.

As discussed above, the femoral head 220 may suitably be identical in design to the femoral head 20 of FIG. 2, and includes an outer surface 238 with an annular protrusion 240 configured to be received by the channel 236.

FIG. 6 shows still another embodiment of the invention in which another bearing component is employed to provide linear rotational movement along a third axis. The embodiment of FIG. 6 is an implant arrangement 310 that includes a femoral head 320 and first liner 314 that are substantially the same as the femoral head 20 and liner 14, respectively, of FIG. 1. The implant arrangement 310 further includes an acetabular shell 312 and a second liner 350.

The acetabular shell 312 includes an outer surface 322 having a generally rounded shape, preferably hemispherical or at least partially spherical. The outer surface 322 is configured to secure to the acetabulum using any well known method and/or structure. The acetabular shell 312 further includes an inner surface 324 that is generally partially spherical in shape.

Along the inner surface 324 is an annular groove or channel 326 that extends generally concentrically with the annular rim 328 of the inner surface 324, about the axis C. The annular groove 326 is located axially inward of the annular rim 328. The channel 326 has a depth that is less than the thickness defined by the distance between the inner surface 324 and the outer surface 322.

As with the acetabular shell 12, the acetabular shell 312 is preferably formed from metal or ceramic. Suitable materials are well known in the art. An exemplary acetabular shell 312 may be constructed of a higher hardness alloy, such as an alloy of cobalt and chromium. For example, the acetabular shell 312 may be constructed of CoCrMo.

The second liner 350 includes an outer surface 352 having a generally hemispherical or at least partially spherical shape which is slightly smaller than the inner surface 324 of the acetabular shell 312. The outer surface 352 is configured to be received by the inner surface 324 of the acetabular shell 312. The second liner 350 also includes an inner surface 354 that has the same general shape, but has a smaller diameter than, the outer surface 352.

The outer surface 352 further includes an outwardly extending annular protrusion 356 that is configured to be received by the annular channel 326 of the acetabular shell 312. In the exemplary embodiment described herein, the annular protrusion 356 extends completely around the outer surface 352 about the axis C, and is axially displaced from the annular rim 358 of the outer surface 352 by approximately the same distance as the distance the channel 326 is axially displaced from the outer rim 328. The annular channel 326 and the annular protrusion 356 cooperate to allow the second liner 350 to rotate at least partially about the axis C.

The inner surface 354 includes an annular groove or channel 360 that extends in an annular linear path about the axis A. The channel 360 has a configuration substantially similar to that of the channel 26 of the acetabular shell 12 of FIG. 2. The channel 360 is therefore configured to cooperate with a protrusion 331 on the outer surface 330 of the first liner 314 to allow rotation of the first liner 314 about the axis A.

The second liner 350, like the first liner 314 is preferably formed from a polymeric material. Suitable materials are well known in the art. An exemplary liner may be formed from UHMWPE or highly cross-linked UHMWPE.

The first liner 314 and the femoral head 320 cooperate in the manner described above in connection with the liner 14 and femoral head 20 of FIG. 2 to allow rotation of the first liner 314 about the axis B.

It will be appreciated that each articulating load bearing surface in FIG. 6 is exposed only to linear annular motion, yet these motions are combined to provide full ball and socket motion, and further including axial rotation.

Figure 7:
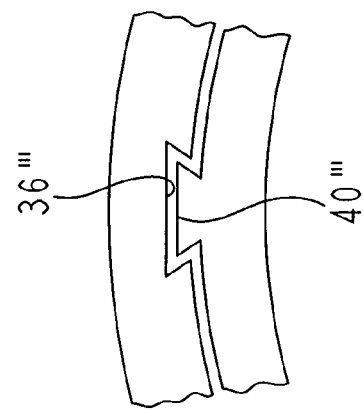
FIG. 7 shows a fragmentary cutaway view of an annular protrusion and corresponding annular groove of the implant arrangement of FIG. 1.

It will also be noted that the annular protrusions of any of FIGS. 1 through 6 may have any number of shapes. FIG. 7 shows an exemplary cutaway cross-sectional view of the annular protrusion 40 disposed within the channel 36 of the implant arrangement of FIG. 2. In this embodiment, the cross section of the annular protrusion is generally rectangular, as is the cross section of the channel 36.

Figure 8:
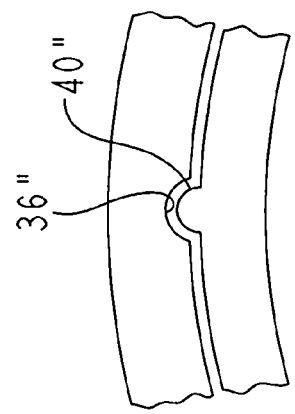
FIG. 8 shows a fragmentary cutaway view of a first exemplary alternative annular protrusion and corresponding annular groove that may be used in the implant arrangements of FIGS. 1–6.
Figure 9:
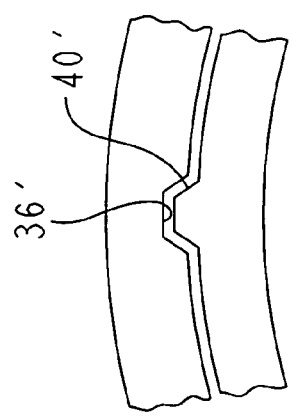
FIG. 9 shows a fragmentary cutaway view of a second exemplary alternative annular protrusion and corresponding annular groove that may be used in the implant arrangements of FIGS. 1–6.

FIG. 8 shows an alternative embodiment of an annular protrusion 40' that is disposed within a channel 36'. The annular protrusion 40' and the channel 36' may be used as an alternative to any protrusion and channel combination in any of FIGS. 1–6. In this alternative embodiment, the annular protrusion 40' and the channel 36' are generally trapezoidal in cross section. FIG. 9 shows another alternative embodiment of an annular protrusion 40" that is disposed within a channel 36" wherein the annular protrusion 40" and the channel 36" are generally semicircular in cross section.

Figure 10:
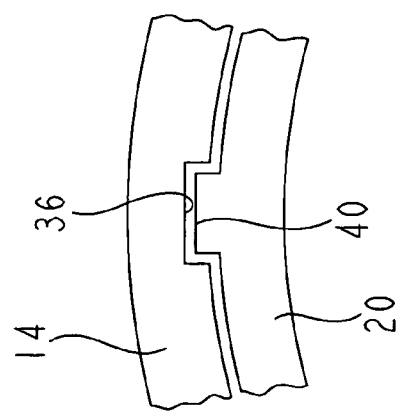
FIG. 10 shows a fragmentary cutaway view of a third exemplary alternative annular protrusion and corresponding annular groove that may be used in the implant arrangements of FIGS. 1–6.

FIG. 10 shows still another embodiment of a protrusion and channel arrangement that may be used in any of the protrusion and channel arrangements of FIGS. 1 through 6. In particular, the annular protrusion 40''' and the channel 36''' have a tongue and groove configuration, or in other words, inverse trapezoidal cross sections. In such an embodiment, the tongue and groove nature of the annular protrusion 40''' and the channel 36''' helps retain and secure together the two bearing components on which they are located. As a consequence, such an embodiment may eliminate the need to use the annular rims 38 and 34 of inner surfaces 24 and 32, respectively, to secure the bearing components together. In particular, as discussed above, the surfaces 24 and 32 are configured to be more than hemispherical so that their corresponding annular rims 28 and 34 could retain the adjacent bearing component.

It is further noted that in some cases, hip implants employ multiple liners for various reasons, such as to allow for modular spacing and sizing, to provide angle offsets, and for other reasons. It will be appreciated that an additional liner may readily be implemented within any of the embodiments described above without departing from the spirit of invention. To this end, an additional liner may be interposed between any two components of any of implant arrangements of FIGS. 1 through 6. The additional liner would presumably connect statically to one of the components and have a channel or groove that cooperates with the corresponding structure on the other adjacent component to create a moveable bearing surface with that other component.

It will be appreciated that the above describe embodiments are merely exemplary, and that those of ordinary skill in the art may readily devise their own implementations and variations that incorporate the principles of the present invention and fall within the spirit and scope thereof.

I claim:

1. A prosthetic implant comprising:
   a first component configured to be disposed within the acetabulum;
   a second component in a load bearing relationship with the first component, the second component operable to rotate relative to the first component about a first axis of rotation, the second component inhibited from movement relative to the first component about a second axis of rotation; and
   a third component in a load bearing relationship with the second component, the third component operable to rotate relative to the second component about the second axis of rotation and inhibited from movement relative to the second component about the first axis of rotation;
   wherein the third component is configured to be supported on femoral bone tissue and comprises a femoral implant head and further comprises a femoral implant stem coupled to the femoral implant head.

2. The prosthetic implant of claim 1, wherein the first component comprises an acetabular shell.

3. The prosthetic implant of claim 2, wherein the second component comprises a liner received at least in part by the acetabular shell.

4. The prosthetic implant of claim 2, wherein the second component comprises a liner, the liner including a cavity, the cavity receiving at least in part the femoral head.

5. The prosthetic implant of claim 1 wherein the first component includes a first feature on an inner surface thereof, and the second component includes a second feature on an outer surface thereof, the second feature received by the first feature, the second feature and the first feature cooperating to inhibit movement in a direction other than the first axis of rotation.

6. The prosthetic implant of claim 5 wherein the first feature is an annular groove, and the second feature is disposed within the annular groove.

7. The prosthetic implant of claim 6 wherein the second feature is a protrusion extending at least partially in an annular direction and having a rectangular cross section.

8. The prosthetic implant of claim 6 wherein the second feature is a protrusion extending at least partially in an annular direction and having a dovetail cross section.

9. The prosthetic implant of claim 1 the first component includes a groove on an inner surface thereof, and the second component includes a pin disposed on an outer surface thereof, the pin received by the groove, the pin rotationally moveable within the groove and annularly moveable within the groove about the first axis of rotation.

10. The prosthetic implant of claim 1 further comprising a fourth component configured to be disposed between the third component and the femoral bone tissue.

11. The prosthetic implant of claim 10 wherein the fourth component is configured to rotate about a third axis with respect to the first component, and inhibited from movement in the first axis of rotation and the second axis of rotation.

12. The prosthetic implant of claim 1, wherein the first axis of rotation and second axis of rotation are perpendicular.

13. The prosthetic implant of claim 1 wherein the second component is constructed of ultra high molecular weight polyethylene.

14. The prosthetic implant of claim 1 wherein the second component includes a first feature configured to engage a feature on the first component to enable movement in the first axis of rotation and includes a second feature configured to engage a feature on the third component to enable movement of the third component in the second axis of rotation.

15. An implant comprising:
a first component comprising an acetabular shell;
a second component comprising liner; and
a third component comprising a femoral head component;
wherein at least two of the first, second and third components include annular grooves, each annular groove receives at least one protruding feature of an adjacent one of the first, second, and third components to allow turning movement of the at least one protruding feature within the groove, and the annular grooves have non-parallel axes of rotation.

16. The implant of claim 15 wherein the liner is constructed of ultra high molecular weight polyethylene.